(12) United States Patent
Campbell

(10) Patent No.: US 12,350,279 B2
(45) Date of Patent: Jul. 8, 2025

(54) NASAL RINSE COMPOSITIONS AND METHODS

(71) Applicant: Campbell Holding Company LLC, Savannah, GA (US)

(72) Inventor: Adam Campbell, Savannah, GA (US)

(73) Assignee: Campbell Holdings Company LLC, Savannah, GA (US)

( * ) Notice: Subject to any disclaimer, the term of this patent is extended or adjusted under 35 U.S.C. 154(b) by 2 days.

(21) Appl. No.: 18/307,112

(22) Filed: Apr. 26, 2023

(65) Prior Publication Data

US 2023/0338400 A1    Oct. 26, 2023

Related U.S. Application Data

(60) Provisional application No. 63/334,918, filed on Apr. 26, 2022.

(51) Int. Cl.
| | | |
|---|---|---|
| *A61K 31/00* | (2006.01) | |
| *A61K 9/00* | (2006.01) | |
| *A61K 9/08* | (2006.01) | |
| *A61K 9/16* | (2006.01) | |

(52) U.S. Cl.
CPC .......... *A61K 31/658* (2023.05); *A61K 9/0043* (2013.01); *A61K 9/08* (2013.01); *A61K 9/1611* (2013.01)

(58) Field of Classification Search
CPC ...... A61K 9/0043; A61K 31/658; A61K 9/08; A61K 9/1611

USPC .......................................................... 514/729
See application file for complete search history.

(56) References Cited

U.S. PATENT DOCUMENTS

| | | | |
|---|---|---|---|
| 7,029,705 B2 | 4/2006 | Fuhr | |
| 9,907,823 B1 * | 3/2018 | Kuhrts | ................ A61K 9/0014 |
| 10,913,729 B2 | 2/2021 | Koch et al. | |
| 10,945,982 B1 | 3/2021 | Lobel | |
| 11,110,056 B1 | 9/2021 | Lobel et al. | |
| 2013/0156871 A1 * | 6/2013 | Keller | ..................... A61P 11/02 |
| | | | 424/742 |
| 2019/0388342 A1 | 12/2019 | Sung et al. | |
| 2020/0215137 A1 | 7/2020 | Speier | |
| 2020/0345585 A1 | 11/2020 | Dresdner, Jr. et al. | |
| 2021/0038513 A1 | 2/2021 | Wilson et al. | |
| 2021/0353667 A1 | 11/2021 | Bishop et al. | |
| 2021/0393576 A1 * | 12/2021 | Wilson | .................... A61P 37/00 |

FOREIGN PATENT DOCUMENTS

TR         201900230 A2 *   6/2020   ............. A61K 33/10

* cited by examiner

*Primary Examiner* — Jeffrey H Murray
*Assistant Examiner* — Rilla Marie Samsell
(74) *Attorney, Agent, or Firm* — Taft Stettinius & Hollister LLP

(57) ABSTRACT

Certain embodiments of the present application relate to a dry composition for preparing a nasal rinse. The dry composition generally includes cannabidiol and a mixture comprising sodium chloride and sodium bicarbonate. In certain forms, the dry composition has less than one percent by weight water. In certain embodiments, the cannabidiol is a water-soluble cannabidiol.

24 Claims, 2 Drawing Sheets

NASAL RINSE COMPOSITIONS AND METHODS

CROSS-REFERENCE TO RELATED APPLICATIONS

The present application claims the benefit of US Provisional Patent Application No. 63/334,918, filed Apr. 26, 2022, the contents of which are incorporated by reference in their entirety.

TECHNICAL FIELD

The present disclosure generally relates to the field of nasal rinses, and more particularly but not exclusively relates to systems and methods for rinsing the nasal sinus cavities.

BACKGROUND

Nasal saline irrigation plays an important role in the treatment of chronic rhinosinusitis, allergic rhinitis and postoperative treatment following endoscopic sinus surgery. Nasal saline irrigation is hypothesized to thin nasal mucous, decrease intranasal membrane edema, improve muco-ciliary clearance and reduce antigen load in the sinus and nasal cavities. High volume nasal saline irrigation has been recommended as Grade A evidence for treatment of chronic rhinosinusitis with and without nasal polyposis by the 2016 International Consensus Statement on Allergy and Rhinology: Rhinosinusitis and the 2012 European Consensus Paper on Rhinosinusitis and Allergy for treatment of chronic rhinosinusitis without nasal polyposis as an adjunct to medical and surgical therapy. A 2016 Cochrane review determined that nasal saline irrigation is strongly recommended given its low risk but potentially beneficial treatment of chronic rhinosinusitis.

Treatment options include low and high-volume delivery options. Low volume delivery options include nasal sprays, pumps and non-mechanical nasal nebulizers. High volume devices have been found to better penetrate the paranasal sinuses. High volume options can either be low or high pressure. Low pressure devices include irrigation bottles or gravity dependent devices while high pressure, high volume devices are often powered. In addition, given their ability to coat the paranasal sinus, nasal saline irrigations are recognized as a useful vehicle for delivery of adjunctive additives to the paranasal sinuses.

In the fields of otolaryngology, allergy, and pulmonology, the "upper airway" is considered the nasal and hypopharyngeal airway while the "lower airway" is considering the trachea and lungs. In the "unified" or "united airway theory" these two anatomic domains are felt to be intrinsically and pathophysiologically linked. Epidemiological and clinical studies have shown a relation between allergic rhinitis, sinusitis and asthma. In addition, asthma severity has been associated with more severe presentation of chronic rhinosinusitis.

Cannabinoids are components of the *Cannabis sativa* plant. Cannabidiol (CBD) is the primary non-psychotropic cannabinoid and is reported to benefit a number of pathologic conditions including inflammatory lung diseases. CBD has been found to exert anti-inflammatory, analgesic and immunomodulatory effects through activation of receptors cannabinoid-1 ($CB_1$) and cannabinoid-2 ($CB_2$). $CB_1$ activation can modulate central nervous system (CNS) neurotransmitter release, while $CB_2$ can modulate release of inflammatory cytokines. Expression of $CB_2$ occurs primarily in peripheral immune modulatory tissues—especially B cells, Natural Killer (NK) cells, as well as T cells and polymorphonuclear cells (PMNs). In animal models, $CB_2$ activation has shown to down-regulate IgE mediated mast cell activation resulting in decreased edema and hyperalgesia. In addition, non-receptor dependent antioxidant effects of CBD have been noted. CBD treatment has been shown to reduce relevant cytokines in animal models of chronic asthma and reduce the inflammatory process both acutely and chronically, including in inflammatory lung disease. In a recent allergic asthma animal model study, CBD administration reduced the inflammatory and remodeling process with decreased airway hyperreactivity secondary to activation of CB 1 and the protective, anti-inflammatory response being complex and possibly not receptor dependent.

*Cannabis* has been well postulated as a possible treatment for pain in neoplastic, inflammatory and neuropathic pain. *Cannabis* is overall well tolerated in human subjects and has been found to have mild adverse effects including dizziness, xerostomia, nausea and fatigue. In animal models, CBD was found to be absorbed within 10 minutes of intranasal application with a bioavailability of 34-46%.

The most beneficial composition of nasal saline for nasal health, treatment of postoperative sinuses or sinusitis is a topic of debate. Both laboratory and clinical studies have tried to answer this question. Hypertonic saline solutions (>0.9%) have been shown to improve mucosal edema and muco-ciliary beat frequency in laboratory studies but have not shown a clear benefit in clinical studies. For these reasons among others, there remains a need for further improvements in this technological field.

SUMMARY

Certain embodiments of the present application relate to a dry composition for preparing a nasal rinse. The dry composition generally includes cannabidiol and a mixture comprising sodium chloride and sodium bicarbonate. In certain forms, the dry composition has less than one percent by weight water. In certain embodiments, the cannabidiol is a water-soluble cannabidiol. Further embodiments, forms, features, and aspects of the present application shall become apparent from the description and figures provided herewith.

DETAILED DESCRIPTION OF ILLUSTRATIVE EMBODIMENTS

Figure 1:
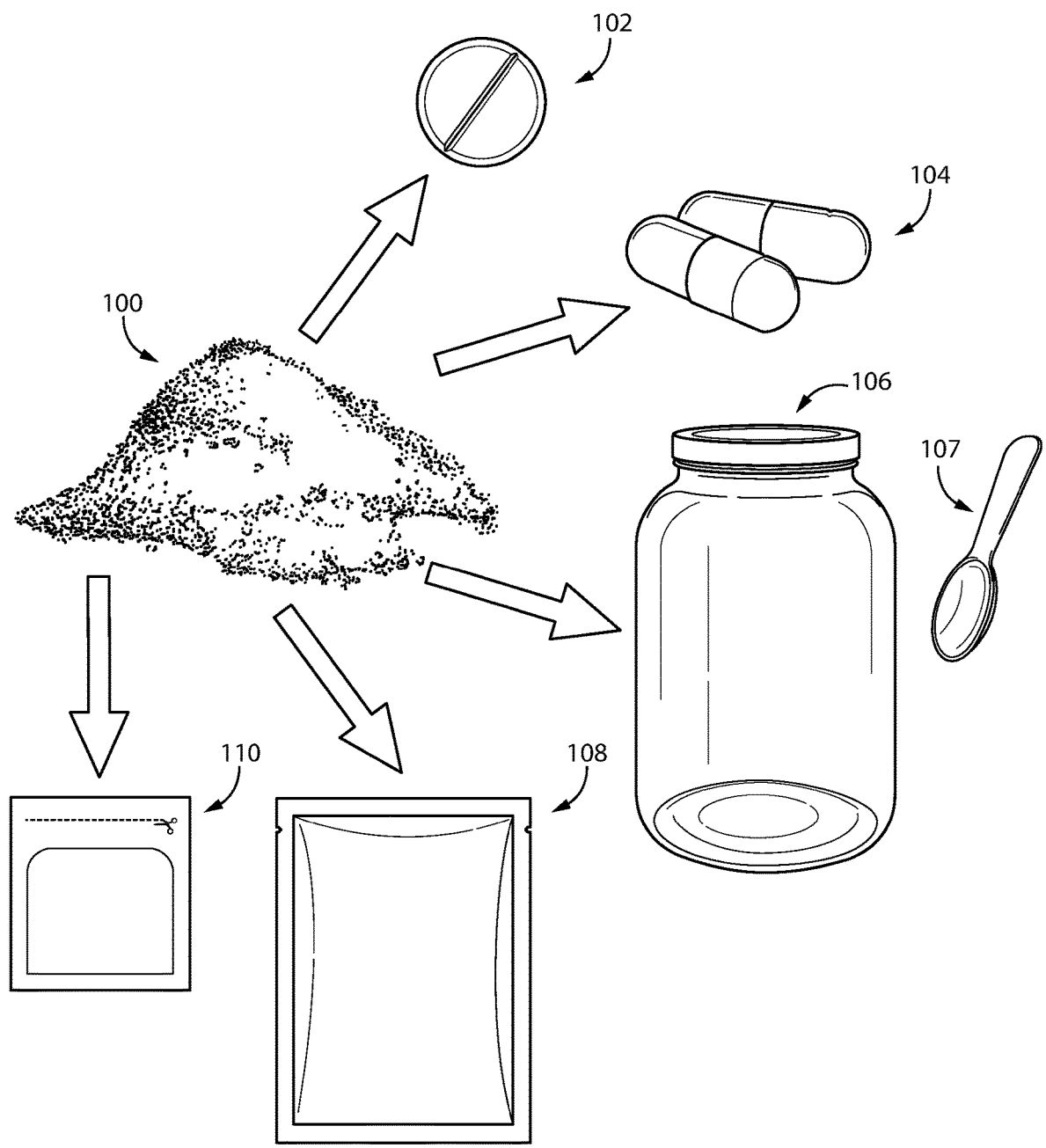
FIG. 1 is a schematic illustration of non-limiting forms for a composition according to certain embodiments.

Although the concepts of the present disclosure are susceptible to various modifications and alternative forms, specific embodiments have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. It should further be appreciated that although reference to a "preferred" component or feature may indicate the desirability of a particular component or feature with respect to an embodiment, the disclosure is not so limiting with respect to other embodiments, which may omit such a component or feature. Further, when a particular feature, structure, or characteristic is described in connection with an embodiment, it is submitted that it is within the knowledge of one skilled in the art to implement such feature, structure, or characteristic in connection with other embodiments whether or not explicitly described.

Additionally, it should be appreciated that items included in a list in the form of "at least one of A, B, and C" can mean (A); (B); (C); (A and B); (B and C); (A and C); or (A, B, and C). Similarly, items listed in the form of "at least one of A, B, or C" can mean (A); (B); (C); (A and B); (B and C); (A and C); or (A, B, and C). Items listed in the form of "A, B, and/or C" can also mean (A); (B); (C); (A and B); (B and C); (A and C); or (A, B, and C). Further, with respect to the claims, the use of words and phrases such as "a," "an," "at least one," and/or "at least one portion" should not be interpreted so as to be limiting to only one such element unless specifically stated to the contrary, and the use of phrases such as "at least a portion" and/or "a portion" should be interpreted as encompassing both embodiments including only a portion of such element and embodiments including the entirety of such element unless specifically stated to the contrary.

In the drawings, some structural or method features may be shown in certain specific arrangements and/or orderings. However, it should be appreciated that such specific arrangements and/or orderings may not necessarily be required. Rather, in some embodiments, such features may be arranged in a different manner and/or order than shown in the illustrative figures unless indicated to the contrary. Additionally, the inclusion of a structural or method feature in a particular figure is not meant to imply that such feature is required in all embodiments and, in some embodiments, may be omitted or may be combined with other features.

As used herein, the term "USP-grade" may be used to denote chemicals, compounds, and compositions that meet or exceed the standards set by United States Pharmacopeia. As used herein, the term "granular" may be used to describe material comprising discrete particles. The term "powdered" may be used to describe granular material with relatively small particles, such as particles with an average diameter of one millimeter or less.

With reference to FIG. 1, certain embodiments of the present application relate to a composition 100 comprising cannabidiol (CBD). More particularly, a composition according to certain embodiments generally includes sodium chloride, sodium bicarbonate, and cannabidiol (e.g., water-soluble cannabidiol). Given the well-established benefits of nasal saline irrigation for patient symptoms and post-operative hygiene, in addition to its ability to be a paranasal sinus delivery system, nasal saline irrigation may be one method of delivery for the composition. It is hypothesized that intranasal administration of topical cannabidiol can result in improved symptoms and quality of life in patients with sinus pain, pressure, nasal congestion, allergic rhinitis, and chronic sinusitis. The formulations disclosed herein are postulated to alleviate one or more conditions, including but not limited to sinus symptoms; post-nasal drip, congestion, and dryness; nasal allergies; common cold; and nasal irritation from occupational dust, fumes, animal dander, grass, pollen, smoke, smog, and house dust.

In certain embodiments, the composition 100 may be formulated such that, when a predetermined quantity of the composition is mixed by a user (e.g., the patient or consumer) with a predetermined amount of water, it will result in an isotonic solution with roughly 0.9% osmolality (e.g., between 0.7% wt sodium chloride and 1.1% wt sodium chloride). In certain forms, the resulting solution may have a pH of approximately 7.4 (e.g., 7.3 to 7.5). Such an isotonic mixture may, for example, be used for less severe symptoms and/or maintenance therapy.

In certain embodiments, the composition may be formulated such that, when a predetermined quantity of the composition is mixed by the consumer with a predetermined amount of water, it will result in a hypertonic solution with an osmolality of 1.8% or greater, or 2.0% or greater. In other words, the hypertonic solution may comprise at least 1.8% wt sodium chloride, or at least 2.0% wt sodium chloride. In certain forms, the resulting solution may have a pH of approximately 7.4 (e.g., 7.3 to 7.5). The hypertonic mixture may, for example, be used for patients with more acute symptoms of congestion and drainage, who may desire more of a drying effect.

In certain embodiments, the composition may be provided in a pre-measured dosage form. By way of example, the composition may be provided in a granular form or as a solid (e.g., as a stick, or as a tablet). A granular (e.g., powdered) form of the composition may be provided in a sachet packet 108 or a capsule 104, which capsule 104 may be configured to dissolve in water. By way of example, about 3.2 grams of the composition 100 may be provided in a packet 110, and the user may be instructed to mix the contents of the packet with about eight fluid ounces (e.g., between seven fluid ounces and nine fluid ounces) of water (e.g., distilled water). As one illustrative formulation, 3.2 grams of composition may include 2300 mg USP-grade sodium chloride, 700 mg USP-grade sodium bicarbonate, and 100 mg water-soluble CBD, with 100 mg or less of other ingredients (e.g., inactive ingredients). Such a dosage, when mixed with eight fluid ounces of water (about 237 g), results in an isotonic solution with an osmolality of about 0.9% wt sodium chloride. If a higher osmolality is desired, a second dosage may be added to the solution. Regardless of whether a second dosage is utilized, the resulting solution may be administered to the nasal cavity as a nasal rinse up to every two hours as needed.

As noted above, certain embodiments of the present application relate to a composition comprising sodium chloride, sodium bicarbonate, and cannabidiol (e.g., water-soluble cannabidiol). Certain embodiments of the composition may include, by weight, one part CBD (e.g., water-soluble CBD) to about thirty parts (e.g., between 20 parts and 40 parts, or between 25 parts and 35 parts) of a mixture comprising sodium chloride and sodium bicarbonate. It is also contemplated that the composition may include more or fewer parts of the mixture per part of water-soluble CBD. For example, the composition may include, by weight, between two parts and 400 parts of the mixture per part of water-soluble CBD. In certain embodiments, the composition may include at least 50% wt the mixture, and up to 50% wt cannabidiol.

The mixture comprising sodium chloride and sodium bicarbonate may comprise, by weight, one part sodium bicarbonate to about three parts (e.g., between 2.5 parts and 3.5 parts) sodium chloride. In certain embodiments, the composition may consist essentially of sodium chloride, sodium bicarbonate, and cannabidiol (e.g., water-soluble cannabidiol). For example, sodium chloride, sodium bicarbonate, and water-soluble cannabidiol may constitute at least 95% of the total weight of the composition, or at least 99% of the total weight of the composition. In certain embodiments, the composition may consist of sodium chloride, sodium bicarbonate, and water soluble cannabidiol.

As noted above, certain embodiments of the present application relate to a pre-measured dosage form of a composition. As one example, a dosage form may, for example, be configured to mix with about eight fluid ounces of water, and may comprise 10 mg to 1,000 mg CBD (e.g., water-soluble CBD), 500 mg to 1,000 mg sodium bicarbonate, and 1,500 mg to 3,500 mg sodium chloride.

In certain embodiments, the composition may not necessarily be provided in a pre-metered dosage form. As one example, a granular (e.g., powdered) form of the composition may be provided in a jar 106 that includes a sufficient amount of the granular composition for several doses. In such forms, the jar 106 may be sold to the end user with a spoon 107 configured to hold a predetermined amount of the granular composition (e.g., the amount intended to be mixed with a predetermined quantity of water).

With continued reference to FIG. 1, illustrated therein are certain non-limiting forms for the composition. In certain embodiments, the composition may be provided in a granular form 100, such as a powdered form. In certain embodiments, the composition may be processed to form a pre-metered dosage in the form of a tablet 102. In certain embodiments, the composition may be provided in a pre-metered dosage in the form of a capsule 104, the shell of which may be water-soluble. In certain embodiments, the composition may be provided in a jar 106, which may optionally be accompanied by a measuring spoon 107 by which a predetermined quantity of the composition may be measured. In certain embodiments, the composition may be provided in a pre-metered dosage in the form of a sachet packet 108. In certain embodiments, the composition may be provided pre-metered dosage in the form of a sealed packet 110. The composition may be provided as a dry composition comprising less than one percent by weight water, less than 0.5% wt moisture, or less than 0.1% wt moisture.

Figure 2:
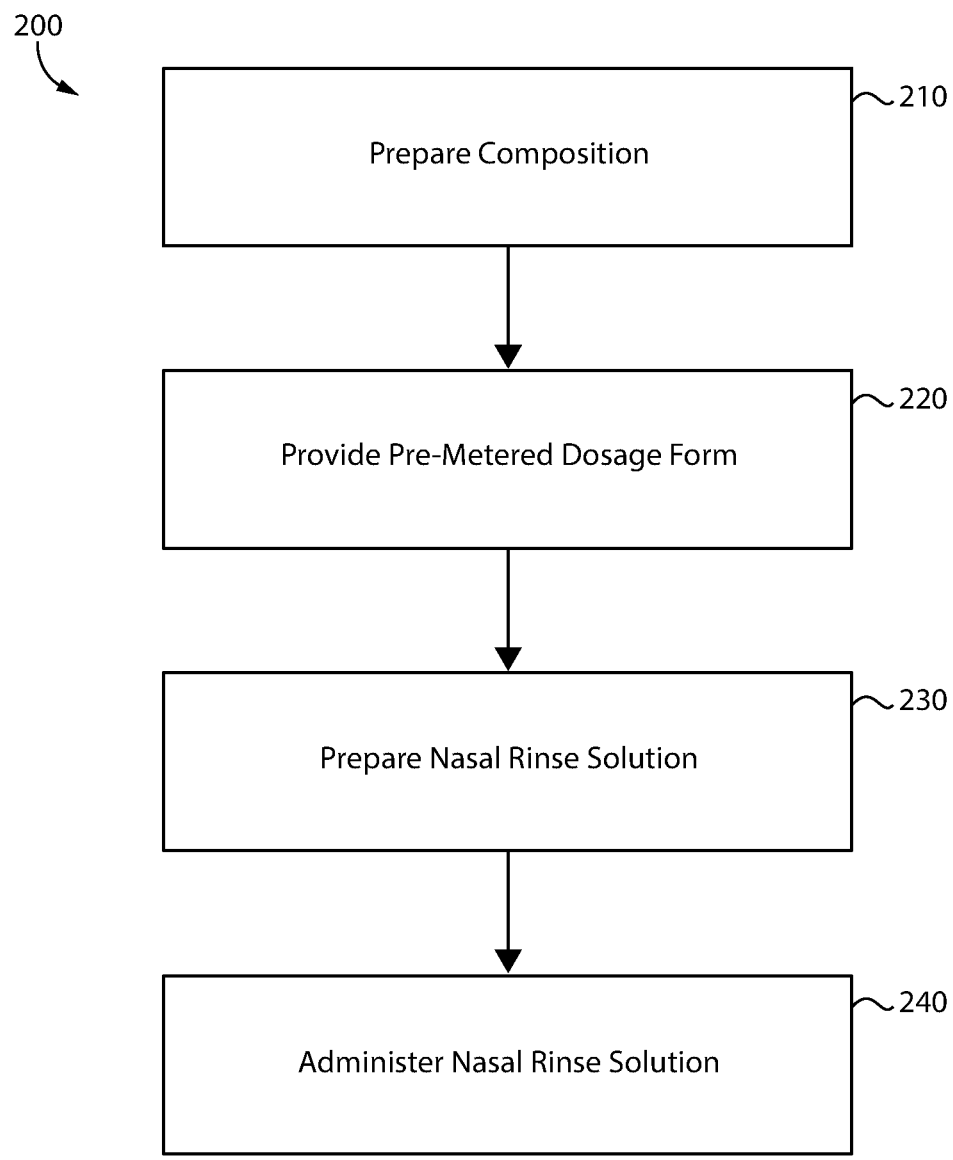
FIG. 2 is a schematic flow diagram of a process according to certain embodiments.

With additional reference to FIG. 2, illustrated therein is a process 200 according to certain embodiments. Blocks illustrated for the processes in the present application are understood to be examples only, and blocks may be combined or divided, and added or removed, as well as re-ordered in whole or in part, unless explicitly stated to the contrary. Additionally, while the blocks are illustrated in a relatively serial fashion, it is to be understood that two or more of the blocks may be performed concurrently or in parallel with one another.

The process 200 may begin with block 210, which generally involves preparing a composition comprising cannabidiol, such as a water-soluble cannabidiol. The composition may further include sodium chloride and/or sodium bicarbonate. The composition prepared in block 210 may, for example, be any of the compositions discussed hereinabove.

In certain embodiments, the process 200 may include block 220, which generally involves providing a pre-metered dosage form of the composition. For example, block 220 may involve providing the composition in a tablet 102, a capsule 104, a sachet packet 108, or a sealed packet 110. In certain embodiments, a pre-metered dosage form of the composition may be provided in a sealed package or pod for use with a powered nasal irrigation system, such as the Naväge® powered nasal irrigation system.

The process 200 may include block 230, which generally involves preparing a nasal rinse solution, including mixing a predetermined quantity of the compound with a predetermined quantity of water. In embodiments in which the composition is provided in a pre-metered dosage form, block 230 may involve adding a predetermined number (e.g., one or two) of the pre-metered dosage forms to the predetermined quantity of water. In certain embodiments, block 230 may involve selecting a desired strength for the nasal rinse solution. For example, if a lower osmolality (e.g., isotonic) solution is desired, block 230 may involve mixing a first predetermined quantity of the compound (e.g., one pre-metered dosage form) with the predetermined quantity of water. As another example, if a higher osmolality (e.g., hypertonic) solution is desired, block 230 may involve mixing a second predetermined quantity of the compound (e.g., two pre-metered dosage forms) with the predetermined quantity of water.

The process 200 may include block 240, which generally involves administering the nasal rinse solution to a nasal cavity. For example, after preparing the nasal rinse solution, the user may administer the solution to his or her nasal cavity using a neti pot, a rinse bottle, an aerosolizer, a syringe, a bulb, or another device suitable for administering nasal rinse solutions. Block 240 may involve irrigating the nasal cavity without requiring that the user/patient hold the solution in the nasal cavity, which can be unpleasant.

While the invention has been illustrated and described in detail in the drawings and foregoing description, the same is to be considered as illustrative and not restrictive in character, it being understood that only the preferred embodiments have been shown and described and that all changes and modifications that come within the spirit of the inventions are desired to be protected.

It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A method, comprising:
   preparing a nasal rinse solution, comprising mixing a first predetermined quantity of a composition with a second predetermined quantity of water, wherein the composition consists essentially of cannabidiol, sodium chloride, and sodium bicarbonate; and
   administering the nasal rinse solution to a nasal cavity.

2. The method of claim 1, wherein the first predetermined quantity of the composition is provided in a pre-measured dosage form.

3. The method of claim 2, wherein the pre-metered dosage form comprises a mixture of the cannabidiol, sodium chloride, and sodium bicarbonate.

4. The method of claim 1, wherein a weight ratio of the first predetermined quantity to the second predetermined quantity is between 1:50 and 1:100.

5. The method of claim 1, wherein the nasal rinse solution is isotonic.

6. The method of claim 1, wherein the nasal rinse solution is hypertonic.

7. The method of claim 1, wherein the cannabidiol is water-soluble cannabidiol.

8. The method of claim 1, wherein the first predetermined quantity of the composition comprises at least 10 mg cannabidiol.

9. The method of claim 1, wherein the composition comprises:
   between 10 milligrams and 1000 milligrams water-soluble cannabidiol;
   between 1000 milligrams and 3000 milligrams sodium chloride; and
   between 500 milligrams and 1000 milligrams sodium bicarbonate.

10. The method of claim 1, wherein the first predetermined quantity of the composition comprises a mixture of the cannabidiol, the sodium chloride, and the sodium bicarbonate prior to mixing with the second predetermined quantity of water.

11. A method, comprising:
   procuring a pre-metered dosage form of a dry composition, the pre-metered dosage form consisting essentially of:
      between 10 milligrams and 1000 milligrams water-soluble cannabidiol;
      between 1000 milligrams and 3000 milligrams sodium chloride; and
      between 500 milligrams and 1000 milligrams sodium bicarbonate;
   mixing the pre-metered dosage form with a predetermined quantity of water to thereby create a nasal rinse solution; and
   administering the nasal rinse solution to a nasal cavity.

12. The method of claim 11, wherein the pre-metered dosage form comprises between 25 milligrams and 250 milligrams cannabidiol.

13. The method of claim 11, wherein the pre-metered dosage form comprises between 2000 milligrams and 2500 milligrams sodium chloride.

14. The method of claim 11, wherein the pre-metered dosage form is a solid form; and
   wherein mixing the pre-metered dosage form with a predetermined quantity of water comprises dissolving the solid form in the predetermined quantity of water.

15. The method of claim 14, wherein the solid form is one of a tablet or a stick.

16. The method of claim 14, wherein the pre-metered dosage form comprises:
   a powder including the water-soluble cannabidiol, the sodium chloride, and the sodium bicarbonate; and
   a capsule in which the powder is contained;
   wherein the capsule is configured to dissolve in water.

17. The method of claim 16, wherein mixing the pre-metered dosage form with the predetermined quantity of water comprises dissolving the capsule in the predetermined quantity of water.

18. The method of claim 11, wherein the nasal rinse solution is isotonic.

19. The method of claim 11, wherein the nasal rinse solution is hypertonic.

20. A method comprising:
   preparing a nasal rinse solution, the preparing comprising mixing a first predetermined quantity of a dry composition with a second predetermined quantity of water, wherein the dry composition is provided in a pre-metered dosage form; and
   administering the nasal rinse solution to a nasal cavity;
   wherein the dry composition comprises water soluble cannabidiol and a mixture of sodium chloride and sodium bicarbonate; and
   wherein a ratio of the water soluble cannabidiol to the mixture of sodium chloride and sodium bicarbonate is between 1:25 and 1:35.

21. The method of claim 20, wherein the mixture comprises, by weight, at least as much of the sodium chloride as of the sodium bicarbonate.

22. The method of claim 20, wherein the mixture comprises between 500 milligrams and 1000 milligrams of the sodium bicarbonate and between 1000 milligrams and 3000 milligrams of the sodium chloride.

23. The method of claim 20, wherein the pre-metered dosage form comprises a sealed package;
   wherein preparing the nasal rinse solution comprises mixing the dry composition with the water using a powered nasal irrigation system; and
   wherein administering the nasal rinse solution comprises administering the nasal rinse solution via the powered nasal irrigation system.

24. The method of claim 20, further comprising selecting the first predetermined quantity based on a desired osmolality of the nasal rinse solution.

\* \* \* \* \*